United States Patent
Fornarelli (10) Patent No.: US 10,420,904 B2
(45) Date of Patent: Sep. 24, 2019

(54) DISPOSABLE TANK AND MOD ASSEMBLY

(71) Applicant: 14th Round Inc., Los Angeles, CA (US)

(72) Inventor: Thomas Fornarelli, Chicago, IL (US)

(73) Assignee: 14th Round Inc., Los Angeles, CA (US)

( * ) Notice: Subject to any disclaimer, the term of this patent is extended or adjusted under 35 U.S.C. 154(b) by 0 days.

(21) Appl. No.: 15/975,929

(22) Filed: May 10, 2018

(65) Prior Publication Data

US 2018/0256835 A1    Sep. 13, 2018

Related U.S. Application Data (63) Continuation of application No. PCT/US2016/061364, filed on Nov. 10, 2016.
(Continued)

(51) Int. Cl.
  *A61M 15/00* (2006.01)
  *A61M 15/06* (2006.01)
  (Continued)

(52) U.S. Cl.
  CPC .......... *A61M 15/06* (2013.01); *A24F 47/008* (2013.01); *A61M 11/042* (2014.02); *A61M 15/002* (2014.02); *A61M 15/008* (2014.02); *A61M 15/0065* (2013.01); *A61M 15/0083* (2014.02); *G08C 17/02* (2013.01); *A61M 15/004* (2014.02); *A61M 15/0035* (2014.02);
  (Continued)

(58) Field of Classification Search
  CPC .. A61M 15/06; A61M 11/042; A61M 15/002; A61M 2205/276; A61M 15/008; A61M 15/0083; A61M 15/0065; A61M 15/0035; A61M 15/004; A61M 2016/0021; A61M 2205/07; A61M 2205/2205; A61M 2205/3368; A61M 2205/3553; A61M 2205/3561; A61M 2205/3569; A61M 2205/3592; A61M 2205/3653; A61M 2205/502; A61M 2205/52; A61M 2205/6018; A61M 2205/6054; A61M 2205/6072; A61M 2205/609; A61M 2205/8206; A24F 47/008; G08C 17/02
  See application file for complete search history.

(56) References Cited

U.S. PATENT DOCUMENTS 3,905,752 A * 9/1975 Miller .................. F23D 11/001
                                                     239/405
6,040,560 A    3/2000 Fleischhauer et al.
(Continued)

FOREIGN PATENT DOCUMENTS

EP    3066942 A1    9/2016
WO    2009118085 A1    10/2009
(Continued)

OTHER PUBLICATIONS

WIPO International Search Authority, International Search Report for PCT/US2016/061364, dated Jan. 23, 2017.

*Primary Examiner* — Steven O Douglas
(74) *Attorney, Agent, or Firm* — Zareefa B. Flener; Flener IP & Business Law (57) ABSTRACT

A disposable medical grade tank and mod assembly for dose controlled smokeless administration of a plurality of vaporized chemicals, and method of use thereof.

20 Claims, 9 Drawing Sheets

Related U.S. Application Data (60) Provisional application No. 62/253,262, filed on Nov. 10, 2015, provisional application No. 62/272,498, filed on Dec. 29, 2015.

(51) Int. Cl.
  *A61M 11/04* (2006.01)
  *A24F 47/00* (2006.01)
  *G08C 17/02* (2006.01)
  *A61M 16/00* (2006.01)

(52) U.S. Cl.
  CPC . *A61M 2016/0021* (2013.01); *A61M 2205/07* (2013.01); *A61M 2205/276* (2013.01); *A61M 2205/3368* (2013.01); *A61M 2205/3553* (2013.01); *A61M 2205/3561* (2013.01); *A61M 2205/3569* (2013.01); *A61M 2205/3592* (2013.01); *A61M 2205/3653* (2013.01); *A61M 2205/502* (2013.01); *A61M 2205/52* (2013.01); *A61M 2205/609* (2013.01); *A61M 2205/6018* (2013.01); *A61M 2205/6054* (2013.01); *A61M 2205/6072* (2013.01); *A61M 2205/8206* (2013.01)

(56) References Cited

U.S. PATENT DOCUMENTS

| | | | | |
|---|---|---|---|---|
| 6,202,642 | B1 * | 3/2001 | McKinnon | A61M 15/009 |
| | | | | 128/200.14 |
| 6,772,756 | B2 * | 8/2004 | Shayan | A61M 11/041 |
| | | | | 128/202.21 |
| 7,186,958 | B1 * | 3/2007 | Nelson | A61M 11/041 |
| | | | | 128/200.23 |
| 7,377,493 | B2 * | 5/2008 | Thomas | A61L 9/12 |
| | | | | 261/121.1 |
| 7,624,734 | B2 | 12/2009 | Balch et al. | |
| 8,016,270 | B2 * | 9/2011 | Chen | F24F 5/0035 |
| | | | | 261/28 |
| 8,056,557 | B2 * | 11/2011 | Lieberman | A61M 11/005 |
| | | | | 128/200.14 |
| 8,739,788 | B2 | 6/2014 | Yomtov | |
| 9,095,175 | B2 | 8/2015 | Terry et al. | |
| 9,360,379 | B2 | 6/2016 | Liu | |
| 10,065,202 | B2 * | 9/2018 | Campbell | B05B 7/2416 |
| 2010/0305958 | A1 | 12/2010 | Shimo et al. | |
| 2011/0108031 | A1 | 5/2011 | Korneff et al. | |
| 2013/0087144 | A1 * | 4/2013 | Todd | A61B 5/1171 |
| | | | | 128/203.14 |
| 2013/0247910 | A1 * | 9/2013 | Postma | A61M 11/041 |
| | | | | 128/203.26 |
| 2014/0014126 | A1 | 1/2014 | Peleg | |
| 2014/0123989 | A1 | 5/2014 | LaMothe | |
| 2014/0202474 | A1 | 7/2014 | Peleg et al. | |
| 2014/0338685 | A1 | 11/2014 | Amir | |
| 2015/0128972 | A1 | 5/2015 | Verleur et al. | |
| 2015/0245656 | A1 | 9/2015 | Memari et al. | |
| 2015/0333561 | A1 | 11/2015 | Alarcon | |
| 2015/0359263 | A1 | 12/2015 | Bellinger | |
| 2016/0053988 | A1 | 2/2016 | Quintana | |
| 2017/0020191 | A1 | 1/2017 | Lamb et al. | |
| 2017/0119058 | A1 * | 5/2017 | Cameron | A24F 47/008 |

FOREIGN PATENT DOCUMENTS

| | | |
|---|---|---|
| WO | 2013128176 A1 | 9/2013 |
| WO | 2014125483 A1 | 8/2014 |
| WO | 2016015264 A1 | 2/2016 |
| WO | 2016029225 A1 | 2/2016 |
| WO | 2016090953 A1 | 6/2016 |
| WO | 2016115890 A1 | 7/2016 |

* cited by examiner

DISPOSABLE TANK AND MOD ASSEMBLY

FIELD OF THE INVENTION

The present invention relates to a disposable tank and mod assembly for providing chemicals for smokeless administration, and a method of using the same. More specifically, the invention relates to an assembly utilizing a disposable tank and a mod with control features for controlling the dosage of administration along with confirming the identity of the user with the tank and the mod medical prescription, and method of using the assembly in smokeless administration of chemicals via vaporization.

SUMMARY OF THE INVENTION

The invention relates to an assembly for providing chemicals for smokeless administration. The assembly includes a disposable tank and a mod. The tank is operable to store a liquid chemical in a liquid container and provide a vapor to a mouthpiece through an air flow passage. The mod receives the disposable tank and includes: an adaptor, a vaporizing element, an intake fan, and an air tube. The adaptor is operable to receive a second end of the tank. The vaporizing element is inside the adaptor and operable to convert the liquid chemical to the vapor. The intake fan is operable to draw air from a plurality of air vents, and the air tube is operable to transport the air from the intake fan to the vaporizing element. The mod of the assembly may further include at least one printed circuit board operating a control system, a plurality of buttons operable to receive input from a user, and a display screen operable to display at least one parameter.

The invention also relates to a mod for dosage control of liquid chemicals. The mod includes a reservoir sleeve, an adaptor, a vaporizing element, an intake fan, and an air tube. The reservoir sleeve receives a first end of a disposable tank, the disposable tank storing a liquid chemical in a liquid container and providing a vapor to a mouthpiece through an air flow passage. The adaptor receives a second end of the disposable tank. The vaporizing element converts the liquid chemical to the vapor. The intake fan draws air from a plurality of air vents, and the air tube transports the air from the intake fan to the adaptor. The mod may further include at least one printed circuit board operating a control system, a plurality of buttons operable to receive input from a user, and a display screen operable to display at least one parameter.

The invention further relates to an assembly having a mod which can control the dosage duration, interval, and count.

The invention further relates an assembly which can recognize the user and correlate the user with the dosage prescription for delivery.

The invention even further relates to a mod which is Bluetooth enabled and able to receive prescription information from a disposable tank, a package, a mobile phone, and a server.

DETAILED DESCRIPTION OF THE DRAWINGS

The following detailed embodiments presented herein are for illustrative purposes. That is, these detailed embodiments are intended to be exemplary of the present invention for the purposes of providing and aiding a person skilled in the pertinent art to readily understand how to make and use of the present invention.

Accordingly, the detailed discussion herein of one or more embodiments is not intended, nor is to be construed, to limit the metes and bounds of the patent protection afforded the present invention, in which the scope of patent protection is intended to be defined by the claims and equivalents thereof. Therefore, embodiments not specifically addressed herein, such as adaptations, variations, modifications, and equivalent arrangements, should be and are considered to be implicitly disclosed by the illustrative embodiments and claims described herein and therefore fall within the scope of the present invention.

Further, it should be understood that, although steps of various claimed methods may be shown and described as being in a sequence or temporal order, the steps of any such method are not limited to being carried out in any sequence or order, absent an indication otherwise. That is, the claimed method steps are considered capable of being carried out in any sequential combination or permutation order while still falling within the scope of the present invention.

Additionally, it is important to note that each term used herein refers to that which a person skilled in the relevant art would understand such term to mean based on the contextual use of such term herein. To the extent that the meaning of a term used herein, as understood by the person skilled in the relevant art based on the contextual use of such term, differs in any way from any particular dictionary definition of such term, it is intended that the meaning of the term as understood by the person skilled in the relevant art should prevail.

Furthermore, a person skilled in the art of reading claimed inventions should understand that "a" and "an" each generally denotes "at least one," but does not exclude a plurality unless the contextual use dictates otherwise. And that the term "or" denotes "at least one of the items," but does not exclude a plurality of items of the list.

Figure 1:
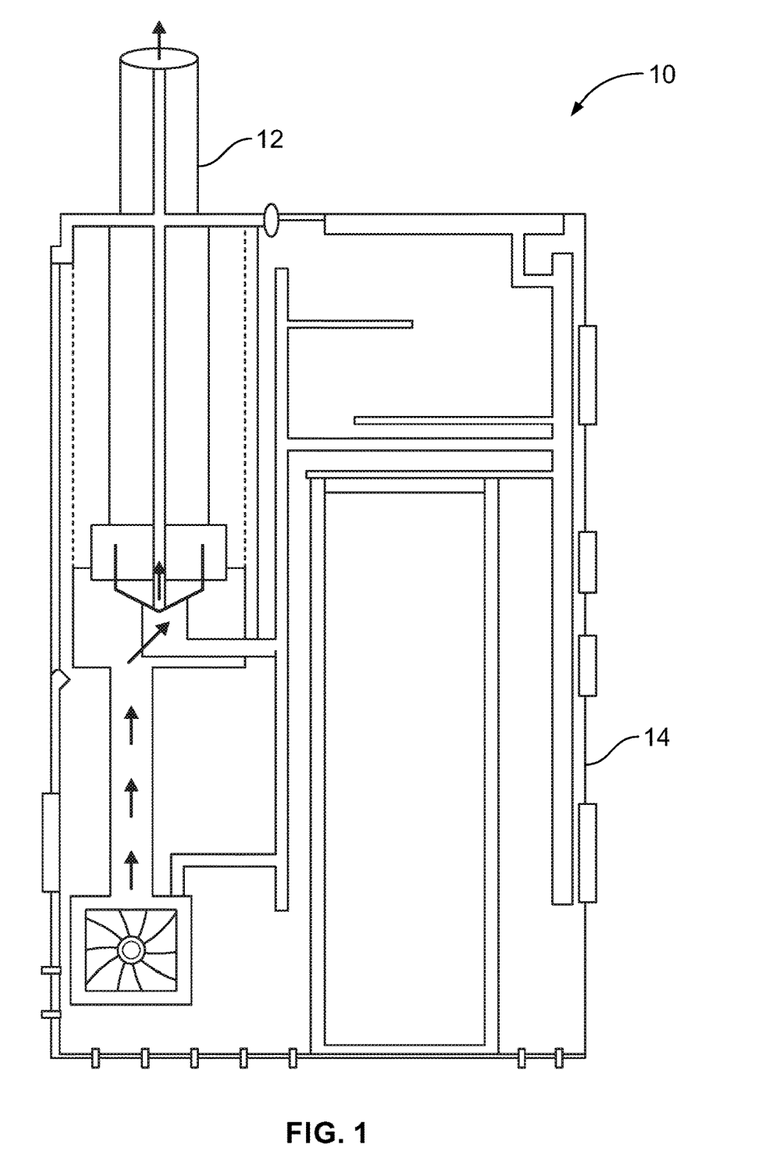
FIG. 1 illustrates an embodiment of the assembly in accordance with the principles of the present invention.

FIG. 1 illustrates the assembly 10 of the invention having a disposable tank 12 and a mod 14. The disposable tank 12 is received by the mod 14. The tank 12 stores a liquid chemical, and the mod converts the liquid chemical to a vapor for delivery through a mouthpiece of the tank 12.

Figure 2:
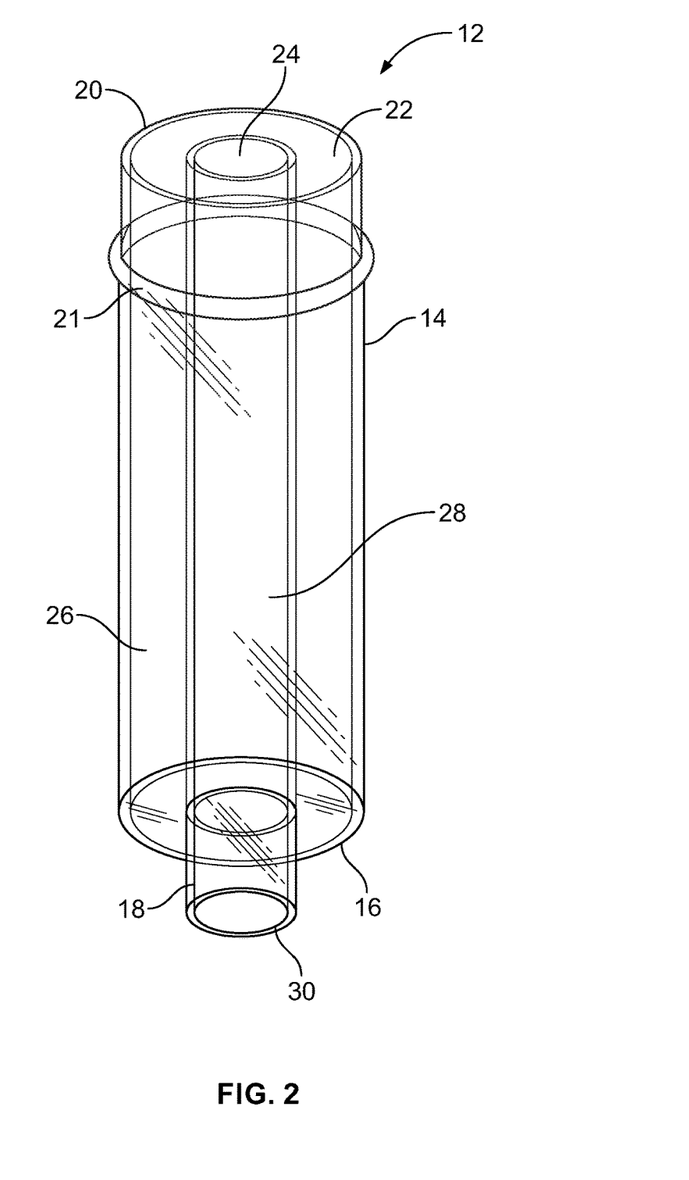
FIG. 2 illustrates an embodiment of the disposable tank of the assembly in accordance with the principles of the present invention.

FIG. 2 illustrates a disposable tank 12 of the assembly 10. The tank 12 has a first tubular portion 14, which abruptly ends, in this particular embodiment, at a 90° degree angle contiguous at a first end 16 with a second tubular portion 18, which is much smaller in diameter than the first tubular portion 14. The second tubular portion 18 terminates at a first end 30. The first tubular portion 14 defines a liquid container 26 and a liquid container aperture 22 located at a second end 20 of the disposable tank 12. The second tubular portion 18 defines an air flow passage 28 and an air passage aperture 24 located at the second end 20. In some embodiments, the first tubular portion 14 includes a plurality of lips 21.

Figure 3A:
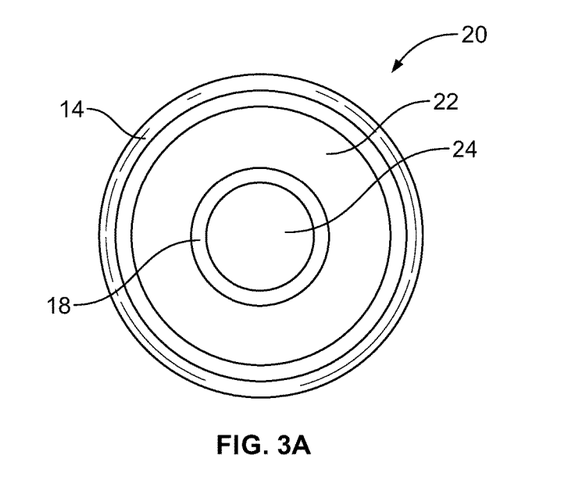
FIG. 3A illustrates an embodiment of the disposable tank of the assembly in accordance with the principles of the present invention.

FIG. 3A illustrates a bottom plan view of the second end 20 of the disposable tank 12. The second tubular portion 18 is housed in the first tubular portion 14. The second tubular portion 18 extends through the first tubular portion 14 to a second end 20 wherein the first tubular portion 14 terminates in the liquid container aperture 22 and the second tubular portion 18 terminates in the air flow aperture 24. The air flow aperture 24 extends through the inside of the disposable tank 12, through the first tubular portion 14, as the air flow passage 28 illustrated in FIG. 2. The liquid container aperture 24 accommodates the liquid chemical in a liquid space 26. The shape and configuration of the first tubular portion 14 and the second tubular portion 18, and therefore the first end 30 and the second end 20, can be of any shape and size. The tubular portions 14, 18 are circular and concentric in this embodiment. Non-circular and non-concentric tubes 14, 18 are also possible. The first tubular portion 14 has a single diameter along its length. In other embodiments, the first tubular portion 14 has a variable diameter.

The liquid chemical can be any liquid chemical including, but not limited to nicotine, cannabidiol, tetrahydrocannabinol, a combination thereof, and/or any other chemicals which are known and understood in the art to be effectively delivered by a vaporization system. The disposable tank 12 is a single component design. In other words, the tank 12 is a coil-less tank, wherein a vaporizing element (also known as a heating coil) generally necessary for vaporizing liquid chemicals is not housed in the tank 12. In this way, an operator can merely use the disposable tank 12 and then discard the tank 12 without wasting any vaporization components. By providing a tank 12 that is of a single component design, no foreign materials outside of the molding materials contaminates the tank. Preferably, the molding materials are a medical grade plastic, but could also be any other material that could be used for this purpose.

The second tubular portion 18 and the first tubular portion 14 is composed of, for example, but not limited to, a glass, a plastic, a metal, an alloy, or a combination of this and other suitable materials known in the art. In a preferred embodiment, the first tubular portion 14 is composed of glass or clear plastic so that a user can see how much liquid is in the liquid chamber 26. In some embodiments, the first tubular portion 14 includes a scale to measure the volume of liquid inside the liquid chamber 26.

Figure 3B:
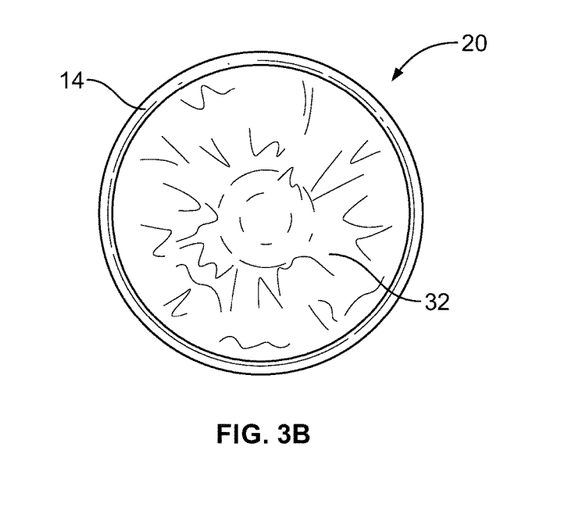
FIG. 3B illustrates an embodiment of the disposable tank with the foil attached in accordance with the principles of the present invention.

FIG. 3B illustrates a bottom plan view of a second end 20 of the disposable tank 12. The second end 20 of the disposable tank 12 is fitted with a foil seal 32 by electromagnetically sealing the foil 32 to the tank 12. Specifically, the foil 32 is applied to the first tubular portion 14 at liquid container aperture 22 and the second tubular portion 18 at the air passage aperture 24, thus covering and hermetically sealing the apertures 22, 24. Methods of applying the foil seal 32 to the tank 12 are well known in the art, for example induction "cap" sealing or capless induction sealing. Induction sealing is a non-contact heating process that hermetically welds a foil laminate (called an inner-seal) to the lip of jars and bottles. The sealing process takes place after the filling (and capping, where the process requires a cap) operation. The FDA recognizes induction sealing as an effective means of tamper evidence. In a preferred embodiment, the foil in the foil seal 32 is a medical grade foil. In other embodiments, the foil seal is a plurality of layers, the plurality of layers including, but not limited to, a foil laminate, a medical grade plastic, an aluminum foil, and a polymer-based foil. This closed system design allows for a tamper proof component structure.

Figure 4:
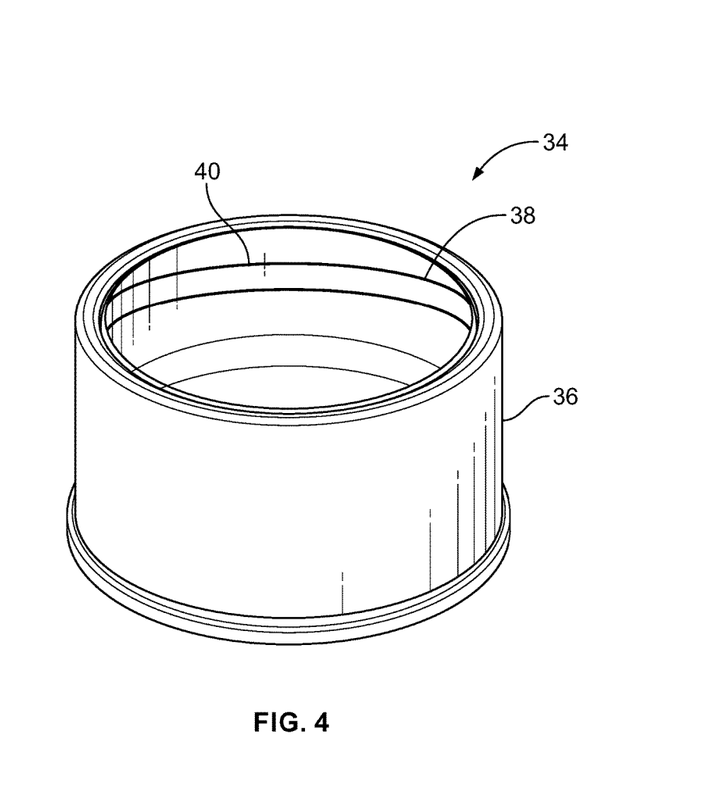
FIG. 4 illustrates an embodiment of the adaptor of the mod of the assembly in accordance with the principles of the present invention.

FIG. 4 illustrates an adaptor 34 of the mod 14. The adaptor 34 has a diameter slightly wider than that of the second end 20 of the tank 12 whereby the adaptor 34 can be fitted over and accommodate the tank 12 in the adaptor aperture 36.

Figure 5:
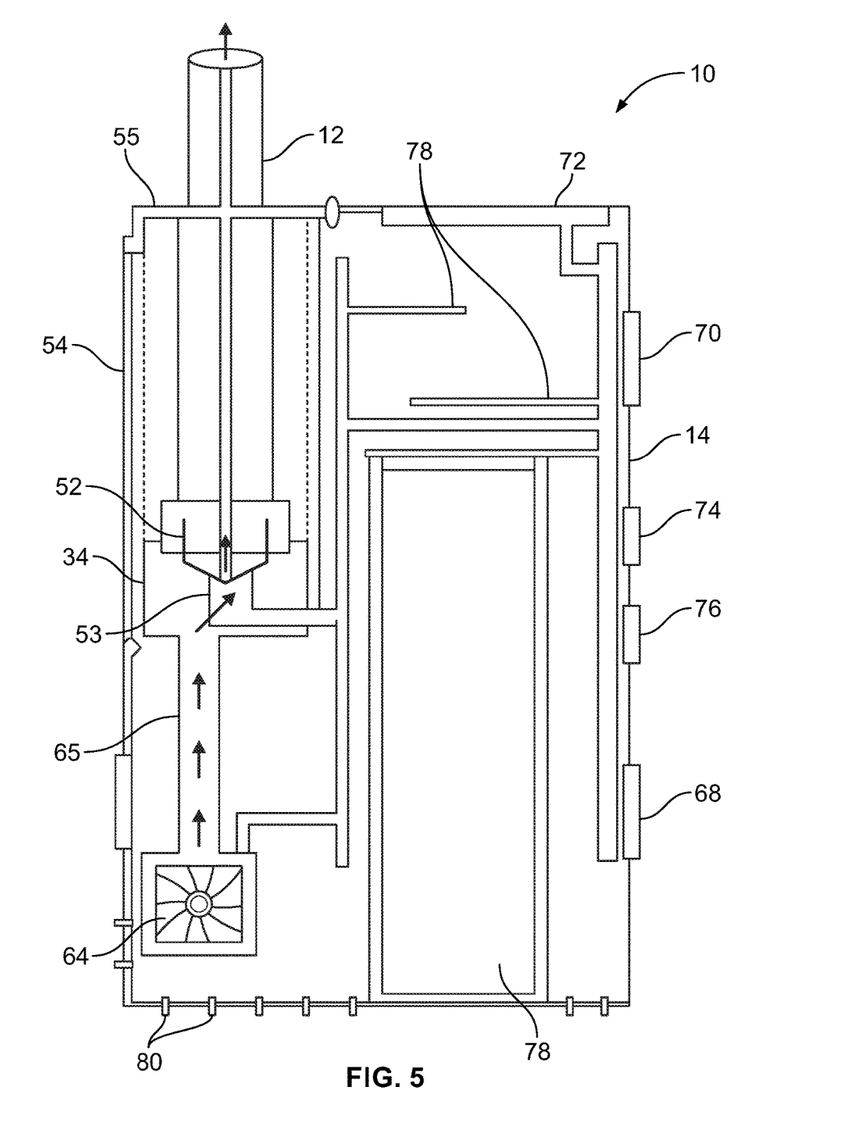
FIG. 5 illustrates a cross section of an embodiment of the mod of the assembly in accordance with the principles of the present invention.
Figure 6:
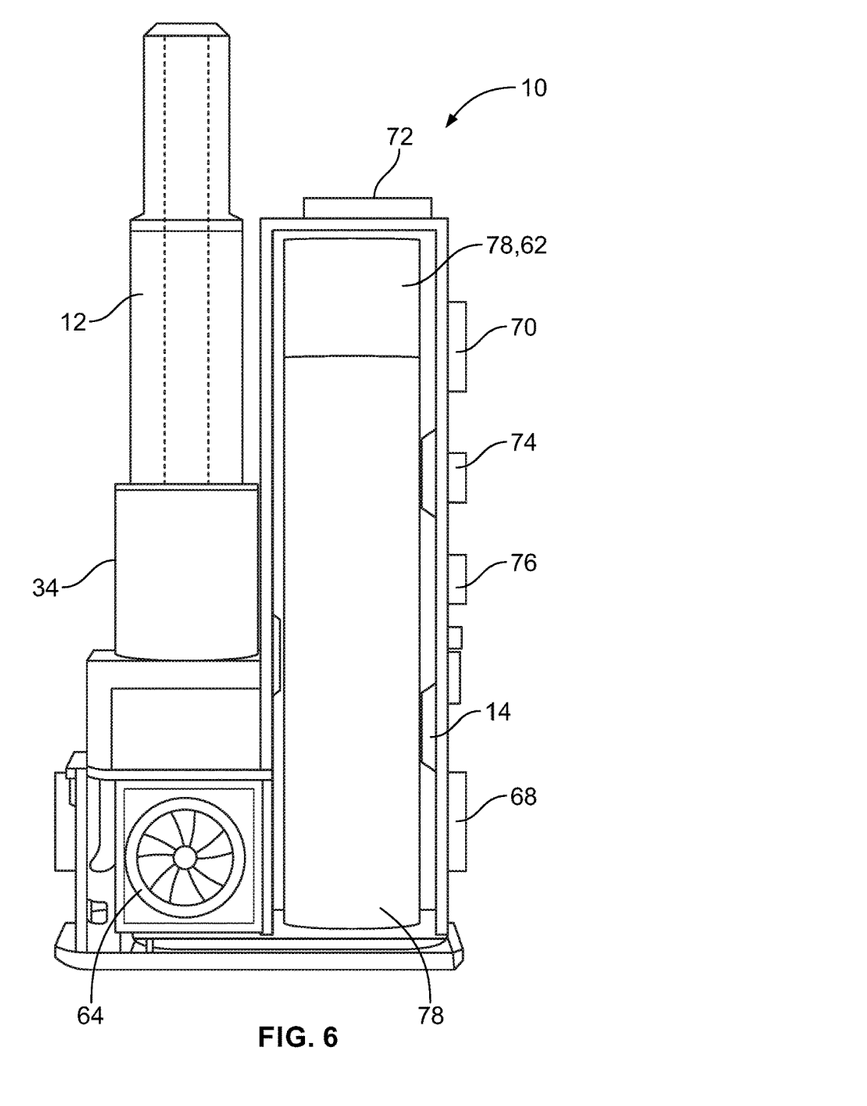
FIG. 6 illustrates a side view of an embodiment of the mod of the assembly in accordance with the principles of the present invention.
Figure 7:
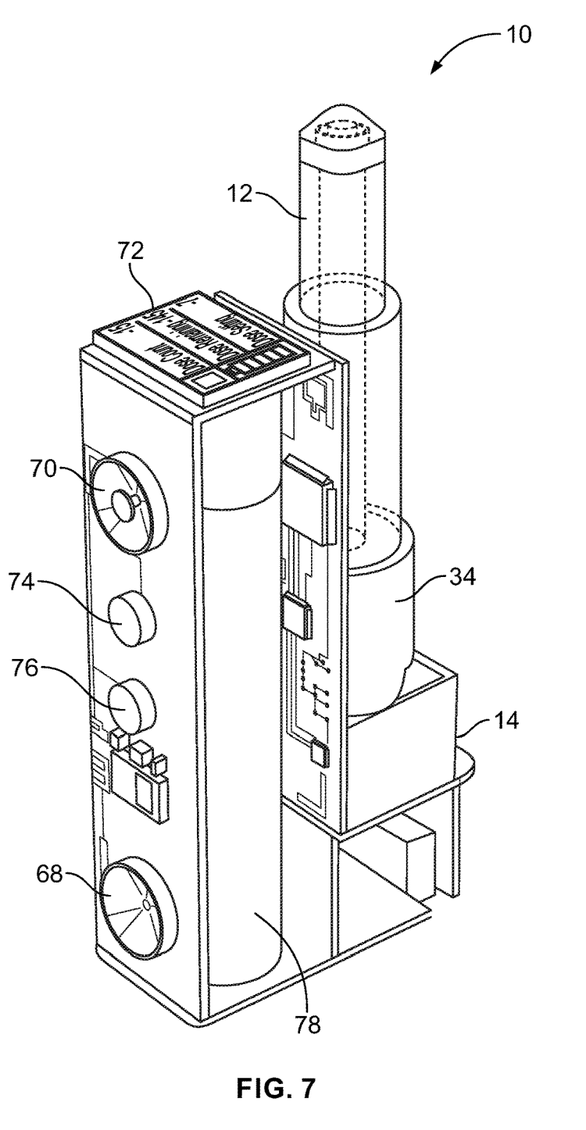
FIG. 7 illustrates a perspective view of an embodiment of the assembly in accordance with the principles of the present invention.
Figure 8:
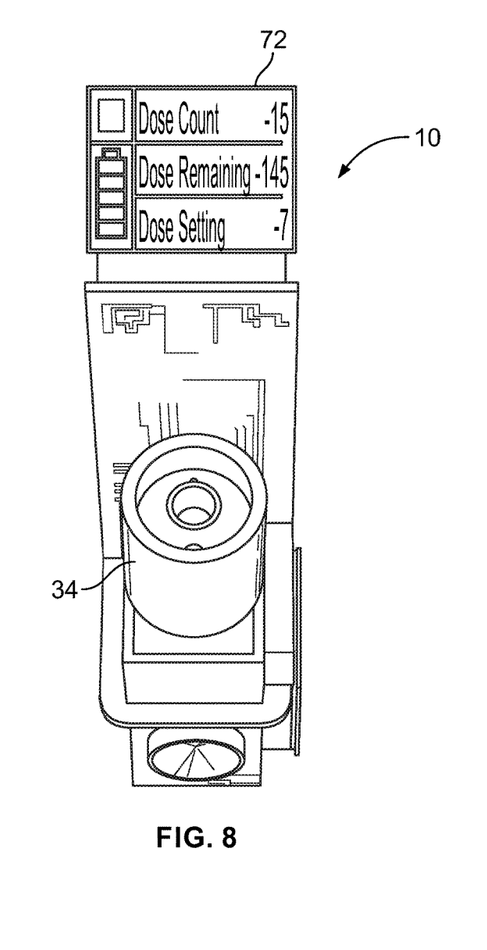
FIG. 8 illustrates a perspective view of an embodiment of the mod of the assembly in accordance with the principles of the present invention.

To provide a more secure fit, the tank 12 can have a plurality of lips 21 to accommodate a plurality of grooves 38 on the adaptor 34. In the alternative, the plurality of lips 21 can be on the adaptor 34 while the plurality of grooves 38 can be on the tank 12. Illustrated in FIG. 3 is a plurality of grooves 38 on an inside wall 40 of the adaptor 34. Correspondingly, the disposable tank 12 has a tank lip 21 surrounding the second end 20 of the tank 12 (see FIG. 2). When the disposable tank 12 is accommodated into the adaptor 34, the lip 21 of the tank 12 accommodates the plurality of grooves 38 on the adaptor 34 thereby securing the tank 12 in place. It is not necessary that the lip 21 be a single lip 21, just as long as the lip 21 is accommodated by the corresponding groove(s) 38. FIG. 5 illustrates a cross-sectional view of the assembly 10 whereby the disposable tank 12 has been accommodated into the adaptor 34 of the mod 14 for operation. FIGS. 6-8 illustrate various views of the assembly 10. The term "mod" of the present invention is intended to cover a broad range of battery powered vaping coils, examples of which include, but not limited to, an advanced personal vaporizer ("APV"), a box mod, and a mod. An embodiment of a mod 14 is shown in FIGS. 5-8.

When assembled, the second end 20 of the tank 12 is accommodated by a reservoir sleeve 54 in the mod 14, as seen in FIG. 5. In use, the tank 12 is inserted into the reservoir sleeve 54 whereby a plurality of piercing elements 52 puncture the foil seal 32, provided in FIG. 5. The plurality of piercing elements 52 are found inside the adaptor 34. These piercing elements 52 deliver the liquid chemicals from the tank 12 to a vaporizing element 53, thereby providing a consistent and even flow of liquid chemicals to the vaporizing element 53. The vaporizing element 53 can be of any material known in the art to effectively heat liquid chemicals, for example, including nickel or a nickel alloy. In some embodiments, the vaporizing element 53 is found inside the adaptor 34. In other embodiments, the vaporizing element 53 is a separate component from the adaptor 34.

When the second end 20 of the tank 12 is received by the adaptor 34, the tank 12 is secured by a reservoir sleeve 54. The reservoir sleeve is also a portion of an outer casing of the mod 14, and may be referred to as the outer casing. The first end 16 of the tank 12 may be received by a hinge door 55 of the reservoir sleeve 54. The hinge door 55 allows a user to remove the tank 12 from the mod 14 with ease. In some embodiments, the hinge door 55 includes a locking mechanism such as, but not limited to, a magnet, a combination lock, and a child-proof lock. The hinge door 55 includes an aperture 56 (shown in FIG. 11) for a portion of the tank 12 to pass through.

In some embodiments, the adaptor 34 does not contain a vaporizing element. Rather, the assembly 10 includes an atomizer rather than a disposable tank. In an embodiment with an atomizer, the vaporizing element is located in the atomizer, and the adaptor 34 includes electrical connections to provide power from the battery 78 to the vaporizing element of the atomizer. The atomizer may also be referred to as, but not limited to, a cartomizer, a clearomizer, and other terms known in the art.

The portion of the inner tubular portion 18 that passes through the aperture 56 is sometimes referred to as a mouthpiece of the tank 12. In some embodiments, additional components may be attached to the tank 12 to serve as an extension or addition to the mouthpiece. Such additions include, but are not limited to, a sanitizer, a guard, and a cleaning cloth.

The adaptor shown in FIG. 5 is describe with respect to FIG. 4. In some embodiments, a threaded portion is used to attach the tank 12 to the adaptor 34 (rather than the lips and grooves described). Use of threaded portions to attach components of the assembly 10 are known to people having ordinary skill in the art.

The mod 14 of the assembly 10 includes an air intake fan 64. The intake fan 64 receives air from a plurality of air vents 80, and the air is transported by an air tube 65 from the fan 64 to the adaptor 34. Air is drawn through the air vents 80 either by powering the fan 64 or a user inhales through the mouthpiece of the tank 12. The shape of the air vents 80 can be any shape which allows air to flow into the intake fan 64 and air tube 65. In some embodiments, the air vents 80 are adjustable, such that they can be partially opened or closed depending on a user's preference. Changing the air vents 80 can, for example, change the temperature of the vapor created by the vaporizing element. In other embodiments, the user is unable to adjust the air vents 80. Rather, a control system 62 adjusts one of the air vents 80 and the intake fan 64 to change the dosage of the liquid chemical. Moreover, the plurality of air vents 80 could be closed while the vaporizing element heats the chemical(s) in the tank, and opened (even partially) for inhalation by a user.

FIG. 5 provides an embodiment of a mod 14 for use in the assembly 10 having a plurality of printed circuit boards ("PCBs") operating a control system 62. The control system 62 can be used to adjust voltage, wattage, frequency, speed, and/or torque of the air intake fan 64. In an embodiment of the control system 62, the mod 14 has both variable voltage and wattage, and therefore the control system adjusts for both. In the alternative, the mod 14 may only have variable voltage or variable wattage, and therefore an embodiment of the control system 62 could also only adjust for one. The mod 14 includes a rechargeable battery 78. The battery 78 may be of a plurality of sizes and voltages, or in the alternative, the mod 14 could have a removable battery. An embodiment of the mod 14 for use in the system 10 of the present invention could also be mechanical whereby the mod merely utilizes a non-adjustable voltage of the battery, whereby the vaporizing element 53 of the system 10 vaporizes the chemicals in the tank 14 at the voltage of the battery. In some embodiments, as shown in FIG. 5, the battery 78 is parallel, adjacent, and non-concentric to the tank 12 within the assembly 10. This layout is more compact than previous assembly designs known in the art.

The control system 62 of the mod 14 of the assembly 10 could also be provided with a temperature adjustment means whereby the temperature to which the vaporizing element 53 (for example, a heating coil) is heated is adjusted depending on the type and form of the chemicals being vaporized. For example, waxes are vaporized at a different temperature from essential oils, which are vaporized at a different temperature than dry herbs. The control system 62 can also be fitted with a timer which can be set to a time for controlling the timing of a vaporizing element 53 in the mod 14 and a fan 64 associated with the mod 14, as well as how fast and for how long the chemicals are delivered to and vaporized by the vaporizing element 53.

In an embodiment of the mod 14 for use in this assembly 10, the fan 64 could further include a piezo electric pump which fits inside the mod 14. Dimensions of the piezo electric pump are, for example, but not limited to, 4 mm×15 mm×8 mm, or 20 mm×20 mm×1.5 mm. In use, such a pump (not shown) could move liquid and/or pump air through the mod 14 and the system 10 whereby vaporized chemicals enter the air flow passage 28 of the disposable tank 12. The air and/or liquid piezo electric pump could also be two separate features which are operationally connected.

The fan 64 is helpful in delivering the vaporized chemical(s) in the correct dosage to the user. This feature provides the user and medical professional with confidence that the medical dosage and prescription is properly administered in the event that the user/patient has restricted breathing and various other reasons for strained abnormal use of lung capacity including lack of energy or lack of lung capacity.

The mod 14 is also provided with three buttons for operation. The buttons include the first button 74, also referred to as the up button 74, and the second button 76, also referred to as the down button 76. In some embodiments, a fingerprint reader 68 (also referred to as a fingerprint button 70). In some embodiments, the buttons 74, 76 are located on opposite sides of the mod so that in use, a user should depress both buttons to activate the mod 14 and/or be recognized as the correct user/patient. The location of the buttons should be ergonomic so that a single user can utilize either a single or both hands to operate the mod 14. The fingerprint reader 70 may also be required to identify a user before operation of the mod 14. The fingerprint reader 70 is security feature to confirm that use of the device resides with a particular user/patient. If a correct user/patient fingerprint (compared to stored fingerprints on a memory of the plurality of PCBs 78) is not received by the reader 70, operation of the assembly 10 is limited. The control system 62 compares the user fingerprint to a stored fingerprint in the memory. The operation may be limited by, for example, but not limited to, no power provided to at least one of the vaporizing element 53 and the intake fan 64.

Also, provided on the mod 14 is an LCD screen 72 for display of the various parameters of the control system 62, including for example, but not limited to, temperature, the duration of time of one puff, the battery power remaining, and the number of puffs. These parameters could be adjustable per the up button 74 and a down button 76. Additionally, operating parameters of the vaporizing element 53 and the air intake fan 64 can be adjusted by the buttons 74, 76 and displayed on the LCD screen 72. Thus, manual adjustments to the operation of the assembly 10 are possible. Operating parameters of the intake fan 64 include, but are not limited to, a fan speed, a fan torque, and a fan frequency. Operating parameters of the electric pump (the piezo-electric air pump or the piezo-electric liquid pump) include, but are not limited to, a pump speed, a pump torque, a pump voltage, and a pump frequency.

However, all the parameters could also be controlled and remotely adjusted by a reader 68. The reader 68 is a way for the assembly 10 to communicate with another device, specifically about prescription information. The reader 68 may be, for example, but not limited to, a radio frequency identification ("RDIF") reader, an infrared ("IR") reader, a Bluetooth reader, and a magnetic strip reader. The reader 68 may be connected and/or part of the plurality of PCBs 78 and control system 62. The reader 68 receives prescription information and/or user identity. The prescription information includes, for example, but is not limited to, a dosage duration, a dosage interval, and a dosage count. The control system 62 adjusts a dosage setting (including, but not limited to, duration, interval, and count) of the assembly 10 based on the prescription information In one embodiment, a RFID or IR reader 68 receives the prescription information from a readable code on the tank 12 (not shown), such as a QR code. In another embodiment, the Bluetooth reader 68 receives the prescription information from a user's mobile device, wherein a medical professional has provided the prescription information to the mobile device. Alternatively, the Bluetooth reader 68 receives the prescription information from a server operated by a medical professional; the Bluetooth reader connects either directly to a server or uses communication modules/networks of a mobile device to connect to the server. In yet another embodiment, the magnetic strip reader 68 receives a portion of a packaging of the tank 12 (or separate piece of material upon which a medical professional has encoded the prescription information).

The reader 68 and the fingerprint button 70 can be used together to ensure a user/patient is taking correct doses of the liquid chemical. Once the user is confirmed via the button 70, the control of the liquid chemical and dosage is set by the control system 62 based on the information received by the reader 68. In one embodiment, a pharmacy could change the prescription information remotely for the mod 14, for example.

The plurality of PCBs 78 and control system 62 include an internal clock (not shown) to properly track the user's prescription and dosage. The internal clock would also have a back-up system so that a particular dose is not missed. The mod 14 is also contemplated to have an alert system to alert a user of the timing of a dose, for example, but not limited to a buzzing created by the mod, or by the LCD screen 72 flashing. The control system 62 contains sensors to detect the user inhaling a dose of the liquid chemical from the assembly 10. Such sensors may include, but are not limited to, an airflow sensor, a pressure sensor, an optical sensor, and a weight sensor. Use of the sensors to detect when the user has inhaled a dose is known in the art.

The plurality of PCBs 78, implementing the control system 62, may include, for example, but not limited to, include a processor, a memory, and a communication module. The modules are connected by one or more control and/or data buses on the PCBs 78. The use of one or more modules and components on the PCBs 78 would be known to a person skilled in the art in view of the present invention described herein.

The processor is, for example, but not limited to, a controller, processor, multiprocessor, microcontroller, or another suitable programmable device. The processor includes a plurality of electrical and electronic components that provide power, operational control, and protection to the components and modules within the assembly. In some embodiments, the processor includes, among other things, a control unit, an arithmetic logic unit ("ALU"), and a plurality of registers, and is implemented using a known computer architecture, such as a modified Harvard architecture, a von Neumann architecture, etc.

The memory of the assembly 10 includes, for example, a program storage area and a data storage area. The program storage area and the data storage area may include combinations of different types of memory, such as read-only memory ("ROM"), random access memory ("RAM") (e.g., dynamic RAM ["DRAM"], synchronous DRAM ["SDRAM"], etc.), electrically erasable programmable read-only memory ("EEPROM"), flash memory, a hard disk, an SD card, or other suitable magnetic, optical, physical, or electronic memory devices. The processor is connected to the memory and executes software instructions that are capable of being stored in a RAM of the memory, for example during execution, a ROM of the memory, for instance on a generally permanent basis, or another non-transitory computer readable medium such as another memory or a disc.

Software for the control system 62 can be stored in the memory. The software includes, for example, firmware, one or more applications, program data, filters, rules, one or more program modules, and other executable instructions. The processor is configured to retrieve from memory and execute, among other things, instructions related to the control processes and methods described herein. Additionally, in some embodiments, the memory may log information related to operation of the assembly 10, such as the time span over which the assembly 10 was operational.

In some embodiments, the memory of the plurality of PCBs 78 is a removable Secure Digital ("SD") card that stores a stored setting. The stored setting is a user feature and/or an actuating interval.

The assembly 10 may communicate with a network 40 via a communication module of the plurality of PCBs 78. The network may be a wireless personal-area-network such as Bluetooth, a wireless wide-area-network such as internet, or a Global Systems for Mobile Communications ("GSM") network. The communication module of the plurality of PCBs 78 may include, but is not limited to, a network chip, an antenna, and the reader 68.

Various ways of controlling the use, the dosage, and the user of the liquid chemical in the tank 12 are provided above. While in one embodiment, the tank 12 is removable and disposable, and can be switched with a different tank under a prescription, in another embodiment there is a lock (not shown) which is activated upon accommodation of a tank keeping the tank 12 in place during operation and until the liquid has been dispensed finally or until a certain level according to a prescription.

If the tank 12 is able to be switched with another tank 12, However, in addition, in such a situation, the control system 62 could be programmed to retain, and the LCD screen 72 to display, dosage information for each tank inserted into the adaptor 34 and the reservoir sleeve 54. Control mechanisms for each such tank would remain in place therefore. One way to control the same would be for the user to manually switch from, for example, tank A to tank B on the mod 14. Another way to control the same would be to switch from A to B remotely and by reader 68 allow the mod 14 to communicate those parameters to the assembly 10. Yet another way to control the same could be a magnetic strip on the tank 12 which when in place, communicates information regarding the prescription, the dosage, and the state of the liquid to the mod upon insertion. These examples are merely examples, and not meant to limit the invention in any way.

Figure 9:
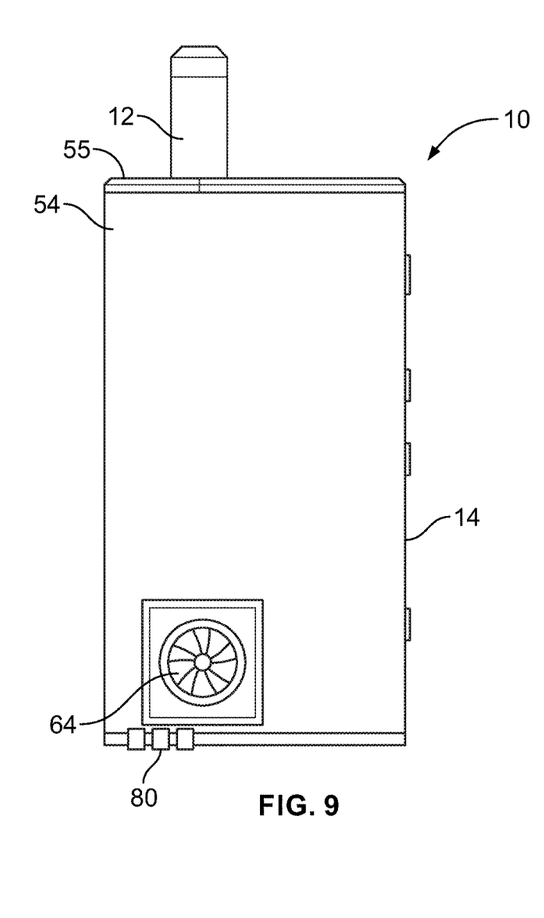
FIG. 9 illustrates a side view of an embodiment of the assembly in accordance with the principles of the present invention.
Figure 10:
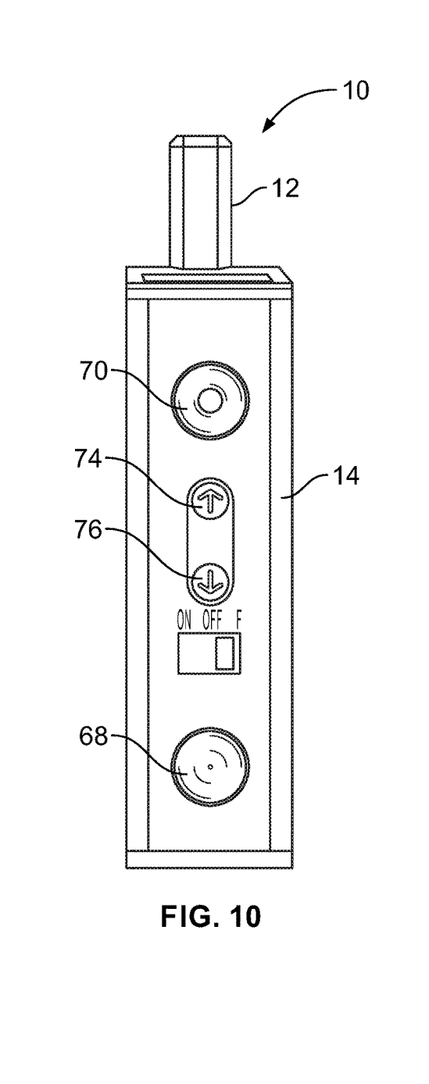
FIG. 10 illustrates a front view of an embodiment of the assembly in accordance with the principles of the present invention.
Figure 11:
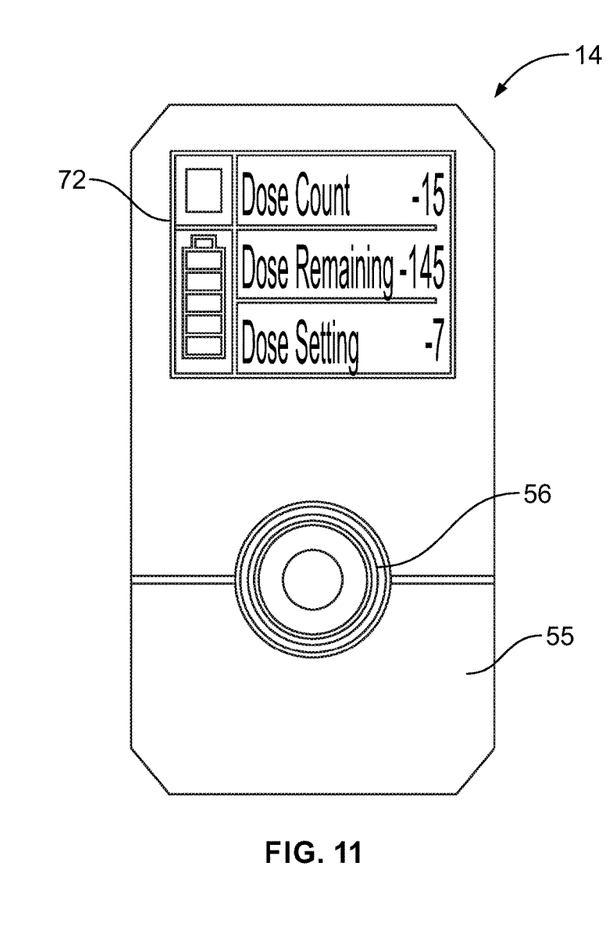
FIG. 11 illustrates a top view of an embodiment of the mode of the assembly in accordance with the principles of the present invention.

FIGS. 6-8 provide additional views and embodiments of the assembly 10 and/or mod 14 (without the outer casing 54 of the mod 14). FIGS. 9-11 also provide additional views and embodiments of the assembly 10 of the present invention.

As to the manner of usage and operation of the present invention, the same should be apparent from the above description. Accordingly, no further discussion relating to the manner of usage and operation will be provided.

While a preferred embodiment of the system has been described in detail, it should be apparent that modifications and variations thereto are possible, all of which fall within the true spirit and scope of the invention. With respect to the above description then, it is to be realized that the optimum dimensional relationships for the parts of the invention, to include variations in size, materials, shape, form, function and manner of operation, assembly and use, are deemed readily apparent to one skilled in the art, and all equivalent relationships to those illustrated in the drawings and described in the specification are intended to be encompassed by the present invention.

Throughout this specification, unless the context requires otherwise, the word "comprise" or variations such as "comprises" or "comprising" or the term "includes" or variations, thereof, or the term "having" or variations thereof will be understood to imply the inclusion of a stated element or integer or group of elements or integers but not the exclusion of any other element or integer or group of elements or integers. In this regard, in construing the claim scope, an embodiment where one or more features is added to any of the claims is to be regarded as within the scope of the invention given that the essential features of the invention as claimed are included in such an embodiment.

Those skilled in the art will appreciate that the invention described herein is susceptible to variations and modifications other than those specifically described. It is to be understood that the invention includes all such variations and modifications that fall within its spirit and scope. The invention also includes all of the steps, features, compositions and compounds referred to or indicated in this specification, individually or collectively, and any and all combinations of any two or more of said steps or features.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. An assembly for providing chemicals for smokeless administration, comprising:
    a disposable tank operable to store a liquid chemical in a liquid container and provide a vapor to a mouthpiece through an air flow passage;
    a mod for receiving the disposable tank, the mod comprising
        an adaptor operable to receive a second end of the tank;
        a vaporizing element inside the adaptor, the vaporizing element operable to convert the liquid chemical to the vapor;
        an intake fan operable to draw air from a plurality of air vents; and
        an air tube operable to transport the air from the intake fan to the vaporizing element.

2. The assembly of claim 1, wherein the mod further comprises a reservoir sleeve operable to secure the disposable tank.

3. The assembly of claim 2, wherein the reservoir sleeve includes a hinged door operable to receive a first end of the disposable tank, and wherein the hinged door includes an aperture for the mouthpiece of the disposable tank.

4. The assembly of claim 1, wherein the mod further comprises a rechargeable battery, and wherein the rechargeable battery is parallel, adjacent, and non-concentric to the disposable tank when the disposable tank is received by the adaptor.

5. The assembly of claim 1, wherein the mod further comprises:
    at least one printed circuit board operating a control system;
    a plurality of buttons operable to receive input from a user; and
    a display screen operable to display at least one parameter.

6. The assembly of claim 5, wherein the input from the user consists of at least one selected from the group consisting of a user identity, a prescription information, and a dosage setting.

7. The assembly of claim 6, wherein one of the plurality of buttons is a fingerprint reader operable to receive a user fingerprint as the user identity, and wherein the control system limits operation of the assembly until the user fingerprint is received at the fingerprint reader and compared to a stored fingerprint.

8. The assembly of claim 6, wherein the mod further comprises a reader selected from the group consisting of a magnetic strip reader, a RFID reader, and a Bluetooth reader.

9. The assembly of claim 8, wherein the reader receives the prescription information from one of the disposable tank and an external device, the external device selected from the group consisting of a packaging, a mobile phone, and a server.

10. The assembly of claim 9, wherein the control system adjusts the dosage setting based on the prescription information received by the reader, wherein the dosage setting is at least one selected from the group of a dosage duration, a dosage interval, and a dosage count.

11. The assembly of claim 6, wherein the control system adjusts an operating parameter of the intake fan based on the prescription information, and wherein the operating parameter of the intake fan is selected from the group consisting of a fan speed, a fan torque, a fan voltage, and a fan frequency.

12. A mod for dosage control of liquid chemicals, comprising:
    an adaptor operable to receive a second end of a disposable tank, the disposable tank storing a liquid chemical in a liquid container and providing a vapor to a mouthpiece through an air flow passage;
    a reservoir sleeve operable to secure the disposable tank;
    a vaporizing element operable to convert the liquid chemical to the vapor;
    an intake fan operable to draw air from a plurality of air vents; and an air tube operable to transport the air from the intake fan to the adaptor.

13. The mod of claim 12, wherein the adaptor includes a plurality of grooves operable to be receive a plurality of lips of the disposable tank.

14. The mod of claim 12, wherein the adaptor includes a piercing element operable to puncture a foil seal of the disposable tank.

15. The mod of claim 12, further comprising
at least one printed circuit board operating a control system;
a plurality of buttons operable to receive input from a user; and
a display screen operable to display at least one parameter.

16. The mod of claim 15, wherein the control system is configured to adjust an operating parameter of at least one selected from the group consisting of a plurality of air vents, the intake fan, the vaporizing element, and a pump based on the input from the user for administering a prescription and dosage parameters.

17. The mod of claim 15, further comprising an electric pump operable to pump air within mod when a user is unable to inhale properly, wherein the control system adjusts an operating parameter of the pump based on the input from the user, and wherein the operating parameter of the pump is selected from the group consisting of a pump speed, a pump torque, a pump voltage, and a pump frequency.

18. The mod of claim 15, wherein one of the plurality of buttons is a fingerprint reader operable to receive a user fingerprint as the user identity, and wherein the control system limits operation of the vaporizing element until the user fingerprint is received at the fingerprint reader and compared to a stored fingerprint.

19. The mod of claim 15, further comprising a reader selected from the group consisting of a magnetic strip reader, a RFID reader, and a Bluetooth reader, wherein the reader receives a prescription information from either the disposable tank or an external device, the external device selected from the group consisting of a packaging, a mobile phone, and a server.

20. The mod of claim 12, wherein the reservoir sleeve includes a hinged door operable to receive a first end of the disposable tank, and wherein the hinged door includes an aperture for the mouthpiece of the disposable tank.

* * * * *